United States Patent [19]

Semm

[11] 4,220,154
[45] Sep. 2, 1980

[54] DEVICE FOR COAGULATING BIOLOGICAL TISSUE

[76] Inventor: Kurt Semm, Hegewischstrasse 4, 23. Kiel 1, Fed. Rep. of Germany

[21] Appl. No.: 813,803

[22] Filed: Jul. 8, 1977

Related U.S. Application Data

[63] Continuation-in-part of Ser. No. 699,305, Jun. 24, 1976, Pat. No. 4,074,719.

[30] Foreign Application Priority Data

Dec. 11, 1976 [DE] Fed. Rep. of Germany ....... 2656278

[51] Int. Cl.$^2$ .............................................. A61B 17/38
[52] U.S. Cl. .................................................. 128/303.1
[58] Field of Search ...................... 128/303.17, 303.13, 128/303.1, DIG. 27, 399–403; 62/55, 49

[56] References Cited

U.S. PATENT DOCUMENTS

| 2,011,169 | 8/1935 | Wappler | 128/303.17 X |
| 2,385,633 | 9/1945 | Lyon | 128/303.1 |
| 3,439,680 | 4/1969 | Thomas | 128/303.1 |
| 3,507,283 | 4/1970 | Thomas | 128/303.1 |
| 3,710,584 | 1/1973 | Leonard | 62/55 X |
| 3,823,718 | 7/1974 | Tromovitch | 128/303.1 |

Primary Examiner—William E. Kamm
Assistant Examiner—Michael H. Thaler
Attorney, Agent, or Firm—Saul Jecies

[57] ABSTRACT

The disclosure is directed to a device for coagulating biological tissue by applying heat to the same. The device has a cooling arrangement by means of which the heating leading end portion which contacts and coagulates the tissue, can be cooled upon completion of the coagulation so that it can be safely withdrawn without causing damage to non-coagulated tissue which it may contact during the withdrawal.

13 Claims, 3 Drawing Figures

DEVICE FOR COAGULATING BIOLOGICAL TISSUE

This is a continuation-in-part of my copending application Ser. No. 699,305, filed June 24, 1976, and now U.S. Pat. No. 4,074,719.

BACKGROUND OF THE INVENTION

This invention relates to devices for coagulating biological tissue by applying heat thereto.

More particularly, the invention relates to a device of the type in question which is provided with a cooling arrangement so that it can be cooled upon completion of the coagulation.

Biological tissue, e.g. the Fallopian Tubes, is coagulated (when necessary) by contacting the tissue with a coagulation instrument, e.g. a coagulation probe, which is electrically heated to a temperature of about 120° to 140° C.

It has been proposed to construct such instruments at their leading end with a stationary jaw and a cooperating movable jaw which together embrace or otherwise grip the tissue to be coagulated. The circuit for the electrical energy required to heat the jaws to coagulation temperature is closed either by a foot contact upon which the surgeon steps until coagulation is completed, or else the circuit is controlled by a timer which is set and which controls the heating operation.

After the predetermined coagulation period is completed the surgeon removes his foot from the switch or the timer mechanism times out; in either case the circuit is interrupted and the leading end portion of the coagulation instrument can now cool off. This, however, is a slow process and it requires a relatively long time before the instrument has cooled down to the temperature of about 40° to 50° which must be reached before the instrument can be safely removed from the coagulated tissue. If the instrument is removed while it is still at a temperature higher than this level, it can damage or otherwise deleteriously influence the non-coagulated tissue with which it comes in contact during its withdrawal from the coagulated tissue. On the other hand, it is undesirable for the surgeon to have to wait so long until the device has sufficiently cooled because he has other steps to perform as part of the surgical procedure.

SUMMARY OF THE INVENTION

It is therefore an object of the invention to avoid the prior-art disadvantages.

More particularly, it is an object of the invention to provide a device for coagulating biological tissue which can be cooled rapidly and safely after the termination of coagulation.

In keeping with these and further objects to become apparent, an aspect of the invention resides in a device for coagulating biological tissue which has first means, including a portion engageable with the tissues to be coagulated, for heating and thereby coagulating the tissue. The device further includes second means for thereafter conducting a cooling fluid to the aforementioned portion of the first means and to the coagulated tissue, so as to cool this portion sufficiently to avoid undesirable influence (e.g. damage) should this portion come into contact with non-coagulated tissue upon its removal from the coagulated tissue.

The invention will now be described with reference to the appended drawings which illustrate preferred embodiments of the invention. However, these should be understood to be exemplary only inasmuch as the scope of the protection sought to obtain is defined exclusively in the claims hereof.

DESCRIPTION OF PREFERRED EMBODIMENTS

Figure 1:
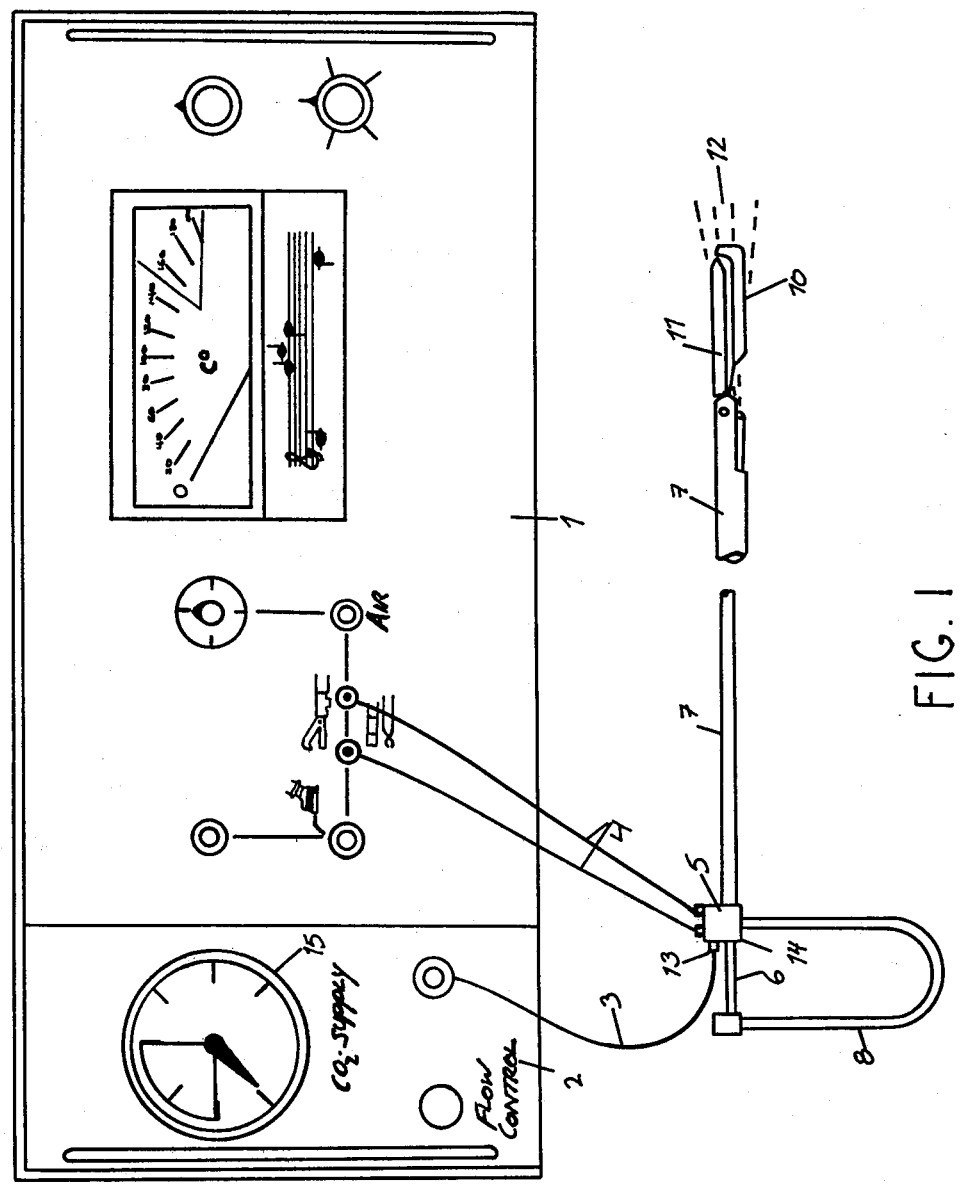
FIG. 1 is a diagrammatic, partly broken-away elevation of a device according to one embodiment of the invention.
Figure 2:
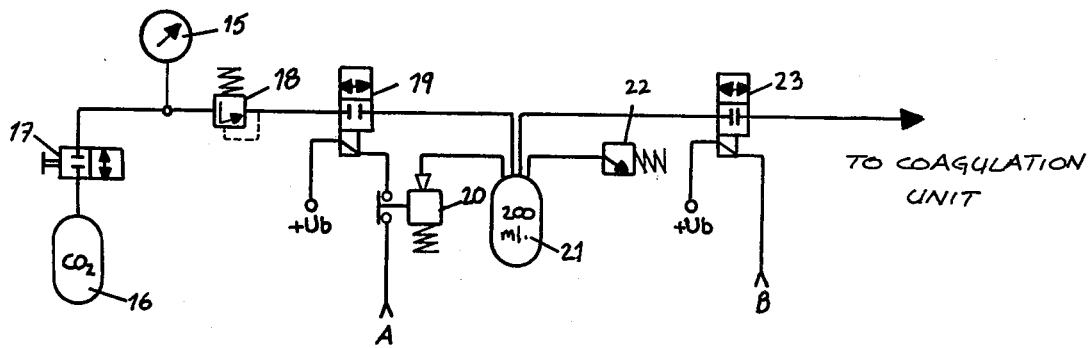
FIG. 2 is a circuit diagram for the device shown in FIG. 1.

One embodiment is illustrated in FIGS. 1 and 2. It shows a coagulation device in form of a gripper-type instrument (other types would also be suitable, e.g. coagulation probes without jaws) having a leading end portion provided with a stationary jaw 10 and with a jaw 11 which is movable with reference to the jaw 10. This movement is effected by means of a control rod 6 which extends through an intermediate tube portion 7 of the device and can slide therein to thereby move the jaw 11. The trailing portion of the device includes a mount 5 at the rear end of the tube portion 7; electrical conductors 4 are connected to the mount 5. How these conductors effect heating of the jaws is not part of the invention and therefore not described.

The mount 5 is also provided with a journal 14 in which the control rod 6 slides. A spring (e.g. leafspring) 8 is connected to and reacts between the mount 5 and the rear end of the control rod 6 which it tends to retract and maintain in the illustrated position.

A nipple 13 is mounted on the mount 5 and communicates with the interior of the tube portion 7. The nipple is connected via a conduit (e.g. a hose) with a source 2 of cooling fluid, here in form of a container (e.g. bottle) which accommodates a gas (e.g. $CO_2$ as shown) under pressure. Such gas travels through tube portion 7 to the jaws 10, 11, cooling the same as the gas issues at 12 (FIG. 1) and also contacts the tissue which has been coagulated by contact with the jaws.

The source 2 automatically furnishes a metered quantity of the cooling fluid (e.g. the gas) at low pressure (e.g. about 1 atmosphere over ambient pressure) to the hose 3 when the coagulation time has ended. The moment at which the gas is so furnished is determined either by the surgeon's removal of his foot from the foot switch which supplies electrical energy for heating via the conductors 4, or by the timing-out of the timer which automatically controls such supply of electrical energy. In the latter case, the necessary electrical contact to effect release of gas from the source 2 will be interposed in the current supply circuit B as shown in FIG. 2.

The source includes (in the illustrated embodiment) a bottle 16 containing e.g. $CO_2$ having a discharge valve 17 and a $CO_2$ content indicator 15. After issuing from the bottle 16 the pressure of the gas is reduced in a pressure reducer to about 1 atmosphere over ambient pressure and the gas is then supplied to an intermediate or metering receptacle 21 having a volumetric capacity of e.g. 200 ml. Filling of the receptacle 21 is controlled by an electromagnetically operated filling valve 19. The operating circuit of the valve 19 is controlled by a pressure switch 20 which is set to interrupt the circuit when the receptacle 21 is filled with e.g. 200 ml gas at about 1 atmosphere pressure. A safety valve 22 at the receptacle 21 prevents an increase of gas pressure therein above the desired level.

Interruption of the circuit of the value 23 at the end of the coagulation period—e.g. due to opening of the foot switch of the device 1 shown in FIG. 1—allows the gas to escape from receptacle 21 and to flow via an indicator 24, the hose 3 and the instrument to the heated jaws 10, 11 in form of a cooling—gas stream 12 which also cools the surrounding tissue. The foot switch is maintained open until the $CO_2$—gas at 1 atmosphere pressure has been vented from receptacle 21. When the pressure in the receptacle drops to zero, the contact of pressure switch 20 closes, thereby opening the filling valve 19 so that the receptacle is filled with $CO_2$ again until the pressure in receptacle 21 builds back up to 1 atmosphere with a resulting interruption of the circuit of valve 19 by the pressure switch 20. It is clear that in this manner there will always be a metered flow of $CO_2$ for cooling the heated jaws and also the surrounding tissues.

FIG. 2 also shows that the electrical current for the electromagnets of the valve 19 as well as of the valve 23, is, in the illustrated embodiment, supplied from the electrical supply source of the device in housing 1 (see the current supply leads A, B in FIG. 2).

Figure 3:
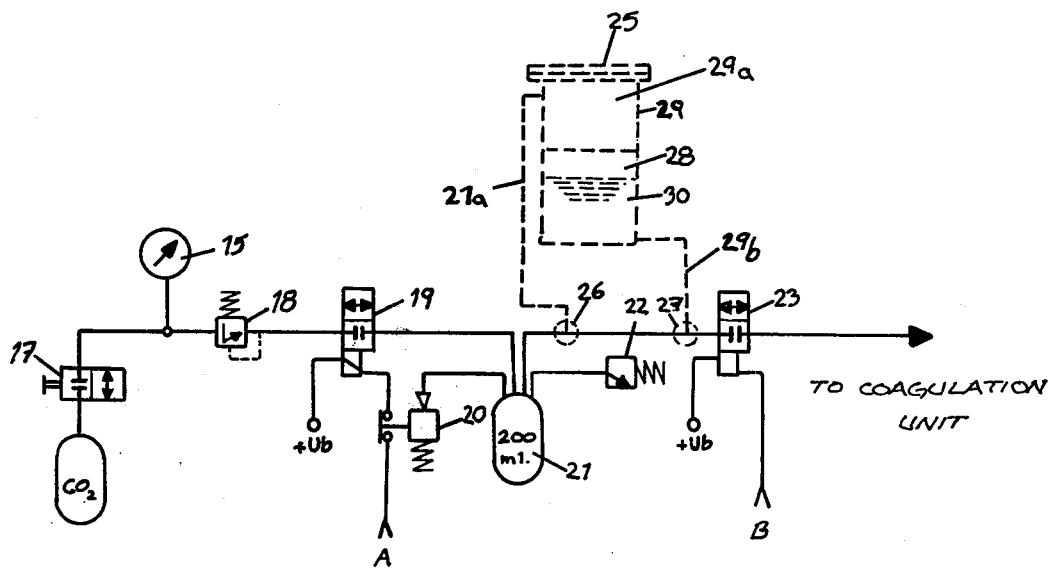
FIG. 3 is a view similar to FIG. 2 but illustrating a modified embodiment.

A further embodiment is illustrated in FIG. 3. This Figure is essentially the same as the embodiments in FIGS. 1 and 2 and, therefore, the same reference numerals have been used to designate identical elements.

FIG. 3 differs from FIGS. 1 and 2 in that an additional source of cooling medium is provided, such cooling medium being a sterile liquid.

It would be conceivable to use sterile liquid in the source 2 of FIGS. 1 and 2, but in FIG. 3 the use of a sterile liquid is illustrated as an addition to the use of a gas, permitting the user of the device the option of using either gas or the sterile liquid (or both in sequence). An additional receptacle 29 is provided in FIG. 3, having a cover 25 which can be closed. Located in the receptacle 29 is a piston 28 which can move towards and away from the sterile liquid (e.g. a sterile saline solution) 30 in the receptacle 29. When the piston moves towards the liquid 30 it expels the liquid from the receptacle 29 which is connected with the flow path intermediate the receptacle 21 and the valve 23. The space 29a in receptacle 29 above the piston 28 therein is connected via a conduit 21a and a portion of the flow path (upstream of valve 23) with the receptacle 21. The space in receptacle 29 which accommodates the liquid 30 is connected with the flow path upstream of the valve 23 by means of a conduit 29b. The pressure in the space 29a is the same as the pressure in receptacle 21 so that the piston 28 presses against the liquid 30 with this same pressure, in the given example with about 1 atmosphere above ambient pressure. If, therefore, the valve 23 is opened after the coagulation is completed, the gas in receptacle 21 presses the piston in receptacle 28 downwardly to expel the sterile liquid 30 via conduit 29b and valve 23 to the jaws 10, 11. The amount of liquid expelled is governed by the time period for which the valve 23 remains open.

The conduits 21a and 29b may be connected with the main flow path by means of two-way valves 26 and 27, respectively, as shown in FIG. 3. In one position these valves will connect the receptacle 21 directly with the valve 23 so that, when the latter is opened, the gas from receptacle 21 will be discharged to the jaws 10, 11. In the other position of the valves 26, 27 the gas from receptacle 21 will be shunted (by valve 26) to the space 29a in receptacle 29 so that, when the cooling is to be effected, the gas will operate the piston 28 and the jaws (and coagulated tissue) will instead be cooled by the expelled sterile liquid 30.

The invention can be variously modified without departing from the spirit and scope of the appended claims. For example, the coagulation instrument need not be of the jaw type which is illustrated; it could be a coagulation probe and the modifications required in that case will offer themselves readily to those skilled in the art.

Although the invention has been illustrated and described with reference to specific embodiments, it is to be understood that these are exemplary only and the scope of protection sought is intended to be governed only by the appended claims.

I claim:

1. In a device for coagulating biological tissue, a combination comprising first means, including a portion engageable with the tissue, for heating and thereby coagulating the tissue:

second means, including a source of cooling fluid, for thereafter conducting cooling fluid from said source to said portion and to the coagulated tissue, so as to cool said portion sufficiently to avoid undesirable influences should said portion come into contact with non-coagulated tissue upon removel from the coagulated tissue, said source comprising a pressurized container including a charge of said cooling fluid in form of a compressed gaseous fluid, a metering receptacle connected with said container and adapted to contain a metered amount of said fluid, an electromagnetic filling valve for admitting said fluid from said container into said receptacle, and means for closing said filling valve when the pressure of fluid in said receptacle reaches a predetermined value said first means comprising a coagulation instrument, said portion constituting a leading end portion of the instrument and the instrument further having a trailing end portion and an intermediate portion which connects said end portions;

said first means further comprising a mount secured to said trailing end portion and thermal energy supplying means connected to said mount for supplying thermal energy via the same to said leading end portion, and said second means also being connected to said mount;

said first mentioned portion further comprising a stationary and a movable jaw, said intermediate portion comprising a tube and said trailing end portion comprising a control rod for said movable jaw extending slidably through said tube and connected to said movable jaw, said mount including a journal which slidably receives a portion of said control rod;

said source of cooling fluid further comprising a nipple on said mount and communicating with the interior of said tube, and a conduit connecting said source with said nipple so that cooling fluid from said source travels via said tube to said stationary and movable jaws.

2. A combination as defined in claim 1, wherein said source supplies said cooling fluid at low pressure so as to avoid damage to the tissue.

3. A combination as defined in claim 1; and comprising means for controlling the supply of a metered quantity of said cooling fluid from said source to said nipple upon elapse of the time required for coagulation of the tissue.

4. A combination as defined in claim 1, wherein said means for closing is a pressure switch calibrated to close said filling valve when the pressure of fluid in said receptacle reaches about 1 atmosphere above ambient pressure.

5. A combination as defined in claim 1, and further comprising a pressure-reducing valve interposed between said container and said receptacle.

6. A combination as defined in claim 5, and further comprising indicating means for indicating the remaining content of gaseous fluid in said container.

7. A combination as defined in claim 6; and further comprising an electromagnetic valve interposed between said receptacle and said leading end portion and arranged to open in response to termination of the coagulation and to remain open until the metered quantity of gaseous fluid has passed from said receptacle to said leading end portion.

8. A combination as defined in claim 7; and further comprising a flow-indicating device interposed in the flow of said gaseous fluid for indicating the flow thereof from said receptacle to said leading end portion.

9. A combination as defined in claim 7, wherein said first means comprises a source of electrical energy, said filling valve and said electromagnetic valve both being connected to said source of electric energy.

10. In a device for coagulating biological tissue, a combination comprising first means, including a portion engageable with the tissue, for heating and thereby coagulating the tissue;

second means, including a source of cooling fluid and a metering receptacle for the same, for thereafter conducting cooling fluid from said source to said portion and to the coagulated tissue, so as to cool said portion sufficiently to avoid undesirable influences should said portion come into contact with non-coagulated tissue upon removal from the coagulated tissue; and a container which accommodates a sterile liquid and a piston movable relative to the liquid so as to expell liquid from the container, said container being connected with the flow path of the cooling fluid at a location downstream of said metering receptacle and means communicating said piston with said metering receptacle so that said piston is subject to the same pressure as the interior of said metering receptacle.

11. A combination as defined in claim 10, and further comprising an electromagnetic valve interposed in said flow path downstream of said location intermediate the same and a leading end of said portion and being arranged to open in response to termination of the coagulation.

12. A combination as defined in claim 11, and further comprising means for connecting said receptacle at the option of a user directly with an electromagnetic valve of said fluid receptacle so that the gaseous fluid from the receptacle travels to said portion, or connecting said receptacle with said piston so that the gaseous fluid in said receptacle moves the piston and causes the same to expel liquid from said container for travel to said portion.

13. A combination as defined in claim 10, wherein said first means comprises a coagulation probe.

* * * * *